United States Patent
Sommer et al.

(10) Patent No.: US 10,416,108 B2
(45) Date of Patent: Sep. 17, 2019

(54) ELECTRODE FOR AN ELECTROCHEMICAL GAS SENSOR, MANUFACTURING METHOD FOR AN ELECTRODE, AND USE OF AN ELECTRODE

(71) Applicant: Dräger Safety AG & Co. KGaA, Lübeck (DE)

(72) Inventors: Sabrina Sommer, Lübeck (DE); Frank Mett, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 291 days.

(21) Appl. No.: 15/311,340

(22) PCT Filed: May 13, 2015

(86) PCT No.: PCT/EP2015/000990
§ 371 (c)(1),
(2) Date: Nov. 15, 2016

(87) PCT Pub. No.: WO2015/172886
PCT Pub. Date: Nov. 19, 2015

(65) Prior Publication Data
US 2017/0082569 A1 Mar. 23, 2017

(30) Foreign Application Priority Data
May 16, 2014 (DE) .......... 10 2014 007 137

(51) Int. Cl.
*G01N 27/404* (2006.01)
*G01N 27/30* (2006.01)
(Continued)

(52) U.S. Cl.
CPC ......... *G01N 27/304* (2013.01); *C01B 32/182* (2017.08); *C01B 32/194* (2017.08);
(Continued)

(58) Field of Classification Search
CPC ............ G01N 27/404; G01N 27/4045; H01M 4/0402; H01M 4/0414–0419
See application file for complete search history.

(56) References Cited

U.S. PATENT DOCUMENTS

| | | | |
|---|---|---|---|
| 8,268,161 B2 * | 9/2012 | Sommer | G01N 27/404 204/431 |
| 2010/0303706 A1 * | 12/2010 | Wallace | B82Y 30/00 423/445 B |

(Continued)

FOREIGN PATENT DOCUMENTS

| | | |
|---|---|---|
| CN | 102227630 A | 10/2011 |
| DE | 195 32 799 A1 | 4/1996 |

(Continued)

OTHER PUBLICATIONS

Ranjbartoreh et al., "Advanced mechanical properties of graphene paper," Journal of Applied Physics 109, 014306 (2011) (Year: 2011).*

(Continued)

*Primary Examiner* — Alexander S Noguerola
(74) *Attorney, Agent, or Firm* — McGlew and Tuttle, P.C.

(57) ABSTRACT

An electrode (100) for an electrochemical gas sensor (1), wherein the electrode has a gas-permeable membrane (4). A graphene layer (3) is applied as an electrode material to the gas-permeable membrane (4). Such an electrode (1) is prepared, for example, by applying a dispersion of graphene or graphene oxide in a volatile liquid to the gas-permeable membrane and evaporating the volatile liquid.

20 Claims, 3 Drawing Sheets

(51) Int. Cl.
*C01B 32/182* (2017.01)
*C01B 32/194* (2017.01)
*H01M 4/04* (2006.01)
*C01B 32/23* (2017.01)

(52) U.S. Cl.
CPC ....... *G01N 27/308* (2013.01); *G01N 27/4045* (2013.01); *C01B 32/23* (2017.08); *H01M 4/0404* (2013.01)

(56) References Cited

U.S. PATENT DOCUMENTS

| | | | |
|---|---|---|---|
| 2013/0156678 A1* | 6/2013 | Banerjee | B82Y 30/00 423/445 R |
| 2013/0192461 A1 | 8/2013 | Miller et al. | |
| 2013/0305927 A1 | 11/2013 | Choi et al. | |
| 2014/0050910 A1* | 2/2014 | Mukherjee | H01M 4/0471 428/219 |
| 2014/0151288 A1* | 6/2014 | Miller | B01D 69/10 210/497.01 |

FOREIGN PATENT DOCUMENTS

| | | |
|---|---|---|
| DE | 198 59 198 A1 | 7/2000 |
| DE | 199 39 011 C1 | 1/2001 |
| DE | 10 2006 014 715 B3 | 6/2007 |
| DE | 10 2006 014 713 B3 | 11/2007 |
| DE | 10 2012 108 305 A1 | 3/2013 |
| GB | 2 342 168 A | 4/2000 |
| WO | 2010/063626 A1 | 6/2010 |
| WO | 2011/159922 A2 | 12/2011 |
| WO | 2013/060773 A1 | 5/2013 |
| WO | 2013/138698 A1 | 9/2013 |

OTHER PUBLICATIONS

Dua et al., "All-Organic Vapor Sensor Using Inkjet-Printed Reduced Graphene Oxide," Angew. Chem. Int. Ed. 2010, 49, 2154-2157 (Year: 2010).*
Nagashio et al., "Mobility Variations in Mono- and Multi-Layer Graphene Films," Applied Physics Express 2 (2009) 025003 (Year: 2009).*
Vikas Berry, "Review—Impermeability of graphene and its applications," Carbon 62 (2013) 1-10 (Year: 2013).*

* cited by examiner

ELECTRODE FOR AN ELECTROCHEMICAL GAS SENSOR, MANUFACTURING METHOD FOR AN ELECTRODE, AND USE OF AN ELECTRODE

CROSS REFERENCE TO RELATED APPLICATIONS

This application is a United States National Phase Application of International Application PCT/EP2015/000990 filed May 13, 2015 and claims the benefit of priority under 35 U.S.C. § 119 of German Patent Application 10 2014 007 137.5 filed May 16, 2014 the entire contents of which are incorporated herein by reference.

FIELD OF THE INVENTION

The present invention pertains to an electrode for an electrochemical gas sensor as well as to a manufacturing method, to the use of such an electrode and to an electrochemical gas sensor with such an electrode.

BACKGROUND OF THE INVENTION

Electrochemical gas sensors are generally known. They usually have a plurality of electrodes, which are in conductive contact with an electrolyte liquid and form in this manner a galvanic cell, hereinafter also called electrochemical measuring cell. Both the composition of the electrolyte liquid and the material of which the electrodes consist are relevant for the specific detection of different analytes. A basic requirement is that the electrodes consist at least partly of a conductive material. In addition to different metals, carbon is therefore also a material of which the electrodes may be manufactured.

The use of diamond-like carbon (DLC) as a measuring electrode material in a gas sensor for toxic gases, for example, $F_2$ or $Cl_2$, is known in this connection from DE 199 39 011 C1. A measuring range to an order of magnitude of about 2 ppm can be covered with such an electrode.

DE 10 2006 014 713 B3 also discloses an electrochemical gas sensor with a carbon-based measuring electrode, namely, with a measuring electrode that comprises carbon nanotubes. This can be used, for example, to detect analytes such as $SO_2$ or diborane. However, there also is a relatively high cross sensitivity to other gases, e.g., $H_2S$ or ozone.

Another prior-art carbon modification is graphene. Even though various different methods are known for manufacturing conductive graphene, e.g., by reducing graphene oxide by means of a camera flash (camera flash method) or by irradiation with UV light, it has not yet been possible to use graphene for manufacturing electrodes that can effectively be used in an electrochemical gas sensor. Even though it is possible by means of a camera flash method to prepare a layer that is conductive on its inside, the surface of the graphene oxide layer is destroyed in the process, so that no reaction is possible with the analytes reaching the layer from the outside. If a method that is gentle for the surface, e.g., irradiation with UV light is used, instead, there is a risk that the reaction will stop after the surface has been converted into graphene and the material located on the inside is not reduced. As a consequence, it is not possible to attain a sufficient conductivity to enable the electrode to be used effectively and in a sufficiently broad measuring range in an electrochemical gas sensor.

SUMMARY OF THE INVENTION

Thus, the basic object of the present invention is to provide an improved electrode for an electrochemical gas sensor. An electrochemical gas sensor, which has such an electrode, shall have the broadest possible measuring range (high measuring range dynamics) and have at the same time the lowest possible cross sensitivity. It is also desirable that the measuring electrode be both able to be used in a flexible manner and processed easily. It is also especially desirable to provide a method for manufacturing such an electrode in which the graphene can be used as an electrode material.

In case of an electrode for an electrochemical gas sensor, the present invention makes provisions for the electrode to have a gas-permeable membrane, wherein a graphene layer is applied to the electrode material on the gas-permeable membrane.

The gas-permeable membrane may be, for example, a porous membrane consisting of polytetrafluoroethylene. However, other membrane materials may be provided as well. For example, the gas-permeable membrane may be a membrane consisting of PFA, FEP, but also Cyclopore®, Isopore or Nucleopore®, consequently polycarbonates or polyesters. The gas-permeable membrane is used as a carrier for the electrode material. The electrode material is typically the component that acts as the electrode in the galvanic cell. The electrode material consists according to the present invention of graphene, which is applied as a layer to the carrier. The graphene may be present both as a single-layer graphene and as a multi-layer graphene. It is especially favorable if the electrode consists exclusively of the gas-permeable membrane and the graphene layer.

It is also advantageous if the graphene is applied from a dispersion to the gas-permeable membrane. In this case both the dispersion may be a dispersion that contains graphene (graphene dispersion) and that the dispersion is a dispersion that contains a graphene precursor, e.g., graphene oxide (graphene oxide dispersion). An electrode obtained in this manner has sufficient conductivity for use in an electrochemical gas sensor. It is favorable in this connection, in particular, if the resistance of the electrode according to the present invention is lower than 10 kΩ and preferably lower than 200Ω.

It was surprisingly found that such an electrode is especially well suited for providing electrochemical sensors with high selectivity and measuring range dynamics. In particular, the cross sensitivity of the sensor can be reduced as well. Such an electrode is also surprisingly robust, so that it can be subjected to further processing without problems without being damaged or losing quality. Furthermore, the electrode according to the present invention is highly insensitive to variations in humidity.

In a first, especially simple embodiment variant, the graphene is in the form of multi-layer graphene. Such an electrode, i.e., an electrode that has a gas-permeable membrane wherein the gas-permeable membrane is coated with multi-layer graphene, preferably has a light gray to dark gray color. It can be prepared, for example, by dispersing graphene powder available at a low cost in a volatile liquid (dispersing agent) and pouring it over a gas-permeable membrane. The dispersing agent will subsequently evaporate. A uniform thin layer of multi-layer graphene is formed on the membrane in the process. It is seen that the electrode according to the present invention may thus be an electrode that has a gas-permeable membrane, wherein the gas-permeable membrane has a graphene layer as an electrode material and wherein the graphene layer is prepared by a method that comprises the steps of a) Dispersing graphene powder in a volatile liquid,
b) Applying the graphene dispersion prepared in step a) to the gas-permeable membrane, and c) Evaporating the volatile liquid.

The graphene dispersion used in step b) is prepared by dispersing graphene powder corresponding to step a). The volatile liquid may be any volatile liquid, provided that graphene and/or graphene oxide can be dispersed in it, for example, it may be water in a very simple case. An organic solvent e.g., propyl alcohol, may be added and/or used.

It is also advantageous if the graphene layer applied to the gas-permeable membrane consists of reduced graphene oxide. For example, the graphene, which forms the graphene layer, may be a graphene that was formed by the reduction of graphene oxide by means of hydrazine or hydrogen iodide or of a mixture of hydrazine and hydrogen iodide. The reduction of the graphene oxide into graphene may take place before, during or after the deposition of the layer on the carrier, i.e., the gas-permeable membrane.

For example, the graphene on the gas-permeable membrane may be graphene that is prepared by applying an aqueous graphene oxide dispersion to the gas-permeable membrane and by carrying out a treatment with a reducing agent after the graphene oxide had been deposited on the membrane. The reducing agent may be selected, for example, from among hydrazine, hydrogen iodide and a mixture of hydrazine and hydrogen iodide. In other words, it is favorable if the electrode is prepared by a method that comprises the following steps:
a) Provision of a gas-permeable membrane,
b) Application of a graphene oxide dispersion to the gas-permeable membrane, and
c) Treatment of the graphene oxide applied to the gas-permeable membrane with a reducing agent.

The reducing agent is preferably selected here from the group comprising hydrazine, hydrogen iodide and mixtures containing hydrazine and hydrogen iodide.

The treatment with the reducing agent corresponding to step c) may be carried out in different ways. The gas-permeable membrane, on which the graphene oxide was deposited, may be exposed to a reducing gas, for example, hydrazine, hydrogen iodide or a mixture of the two. As an alternative, the gas-permeable membrane with the graphene oxide located on it may also be placed into a hydrazine and/or hydrogen iodide solution.

The graphene oxide dispersion, which is used in step b), is preferably prepared by dispersing graphene oxide in a volatile liquid. The volatile liquid may be any volatile liquid in this case as well, provided that graphene and/or graphene oxide is dispersible in it, for example, it may be water in a very simple case. An organic solvent, e.g., propyl alcohol, may be added and/or used.

It is seen that the electrode according to the present invention may consequently also be an electrode that has a gas-permeable membrane, wherein the gas-permeable membrane has a graphene layer and wherein the graphene layer can be prepared by the steps of
a) Dispersing graphene oxide in a volatile liquid,
b) Applying the graphene oxide dispersion prepared in step a) to the gas-permeable membrane so that the graphene oxide is deposited as a graphene oxide layer on the gas-permeable layer from the dispersion, and
c) Treating the graphene oxide layer with a reducing agent.

The reducing agent is preferably selected from the group comprising hydrazine, hydrogen iodide and mixtures containing hydrazine and hydrogen iodide in this case as well.

It is also favorable in any case if the step of
b') Concentrating the dispersion
is also carried out as an additional step after step b). The deposition of the graphene oxide on the gas-permeable membrane is supported and promoted in this manner. The concentration of the dispersion may be carried out, for example, by complete or partial evaporation of the volatile liquid until complete desiccation of the dispersion. The gas-permeable membrane treated with the dispersion may also be exposed, for example, to a vacuum. In an especially preferred embodiment, the electrode is consequently an electrode that has a gas-permeable membrane, wherein the gas-permeable membrane has a graphene layer and wherein the graphene layer can be prepared by
a) Dispersing graphene oxide in a volatile liquid (preparation of a graphene oxide dispersion),
b) Applying the graphene oxide dispersion prepared in step a) to the gas-permeable membrane, so that the graphene oxide is deposited as a graphene oxide layer from the dispersion on the gas-permeable membrane, and
b') Concentration of the dispersion, preferably concentration of the dispersion by evaporating the volatile liquid, and
c) Treating of the graphene oxide layer with a reducing agent,
wherein the reducing agent is selected from the group comprising hydrazine, hydrogen iodide and mixtures containing hydrazine and hydrogen iodide.

As an alternative, the graphene oxide dispersion is treated first with a reducing agent and the dispersion thus reduced is subsequently applied to a gas-permeable membrane. In other words, the electrode may also be an electrode that has a gas-permeable membrane, wherein the gas-permeable membrane has a graphene layer as an electrode material and wherein the electrode is prepared by a method that comprises the steps of
a) Dispersing graphene oxide in a volatile liquid,
b) Treating the graphene oxide dispersion with a reducing agent, so that the graphene oxide dispersion is completely or at least partly converted into a graphene dispersion,
c) Applying the dispersion treated corresponding to step b) to the gas-permeable membrane, and
d) Evaporating the volatile liquid.

The reducing agent may also be selected here form the group containing hydrazine, hydrogen iodide and mixtures containing hydrazine and hydrogen iodide.

In any case, the reduced graphene oxide forms a dark gray layer on the gas-permeable membrane. The electrode thus obtained is characterized by excellent conductivity and high abrasion resistance on the membrane.

The present invention makes, furthermore, provisions for a method for manufacturing an electrode according to the present invention comprising the following steps:
a. Provision of a graphene- and/or graphene oxide-containing dispersion, wherein a volatile liquid is used as the dispersing agent,
b. Application of the dispersion to a gas-permeable membrane,
c. Evaporation of the volatile liquid, such that the graphene and/or graphene oxide is deposited as a graphene and/or graphene oxide layer on the gas-permeable layer, and
d. Optionally treatment of the graphene oxide with a reducing agent, wherein steps a., b., c. and d. may optionally be carried out in the order a., b., c., d. or a., d., b., c.

Step d) is optionally carried out only if a graphene oxide-containing material was used as the electrode material in step a. For example, a uniform layer of graphene oxide may first be prepared on the gas-permeable membrane. This layer can then be converted with the reducing agent into a graphene layer. The graphene layer thus obtained is used as the electrode material, while the gas-permeable membrane acts as a carrier for the electrode material.

A first variant of the method according to the present invention consequently provides for the method comprising the steps of
a. Preparing a graphene-containing dispersion, using a volatile liquid as the dispersing agent,
b. Applying the dispersion to a gas-permeable membrane, and
c. Evaporating the volatile liquid such that the graphene is deposited as a graphene layer on the gas-permeable membrane as a graphene layer.

Provisions are made in another variant according to the present invention for the method comprising the steps of
a. Preparing a graphene oxide-containing dispersion, wherein the volatile liquid is used as a dispersing agent.
b. Applying the dispersion to a gas-permeable membrane,
c. Evaporating the volatile liquid such that the graphene oxide is deposited as a graphene oxide layer on the gas-permeable membrane, and
d. Treating the graphene oxide layer with a reducing agent, so that a graphene layer will be formed on the gas-permeable membrane.

Provisions are made in yet another variant according to the present invention for the method comprising the steps of
a. Preparing a graphene oxide-containing dispersion, wherein the volatile liquid is used as a dispersing agent.
d. Treating the graphene oxide with a reducing agent,
b. Applying the dispersion to a gas-permeable membrane,
c. Evaporating the volatile liquid such that the graphene formed from the graphene oxide corresponding to the preceding step d) will be deposited as a graphene layer on the gas-permeable membrane.

As was already described above, the treatment with the reducing agent corresponding to step d. may be carried out, for example, by vapor deposition of the graphene oxide layer. It is preferred if the reducing agent is used as a gas. As an alternative, the gas-permeable membrane with the graphene oxide layer may also be dipped into the reducing agent. It is preferred in this case if the reducing agent is used as a solution. Even if the treatment of the graphene oxide in the dispersion is carried out prior to the application to the gas-permeable membrane, the reducing agent may be used both as a gas and as a solution. It is thus seen in any case that it is favorable if the reducing agent is used in the gaseous state or as a solution.

Further, it surprisingly proved to be especially favorable if the reducing agent is selected from the group comprising hydrazine, hydrogen iodide and mixtures containing hydrazine and hydrogen iodide. Hydrogen iodide or a mixture of hydrazine and hydrogen iodide is especially preferred, and hydrogen iodide is particularly preferred.

The electrode according to the present invention may be used especially advantageously as a measuring electrode in an electrochemical gas sensor. Depending on the more specific composition of the electrolyte, various substances can be detected by means of the gas sensor. For example, it is possible to detect anesthetic gases, e.g., Propofol. Other gases, e.g., chlorine dioxide, may be detected.

Thus, in another aspect, the present invention pertains to the use of an electrode according to the present invention as a measuring electrode in an electrochemical gas sensor. The electrochemical gas sensor may be a gas sensor for determining Propofol. The electrochemical gas sensor may be a gas sensor for determining chlorine dioxide. It is seen that another solution to the above-mentioned object is an electrochemical gas sensor, preferably an electrochemical gas sensor for detecting Propofol and/or chlorine dioxide, wherein the electrochemical gas sensor has at least one electrode according to the present invention as it is described above.

In addition to the use of such an electrochemical gas sensor for detecting Propofol or chlorine dioxide, other gaseous analytes can also be determined with such an electrochemical gas sensor. Depending on the analyte, different electrolytes may be used, optionally with the addition of a mediator. For example, if the electrolyte is selected correspondingly, it is possible to detect hydride gases, e.g., diborane, silane, phosphine or arsine, and it is possible to detect phenols or even gases such as $Cl_2$, $NO_2$, $H_2$, $O_2$, $O_3$, $SO_2$ and many others.

Further features and details appear from the figures and exemplary embodiments described below. It is obvious that these exemplary embodiment are merely exemplary and that further variants and exemplary embodiments will readily appear to the person skilled in the art on the basis of the present description.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
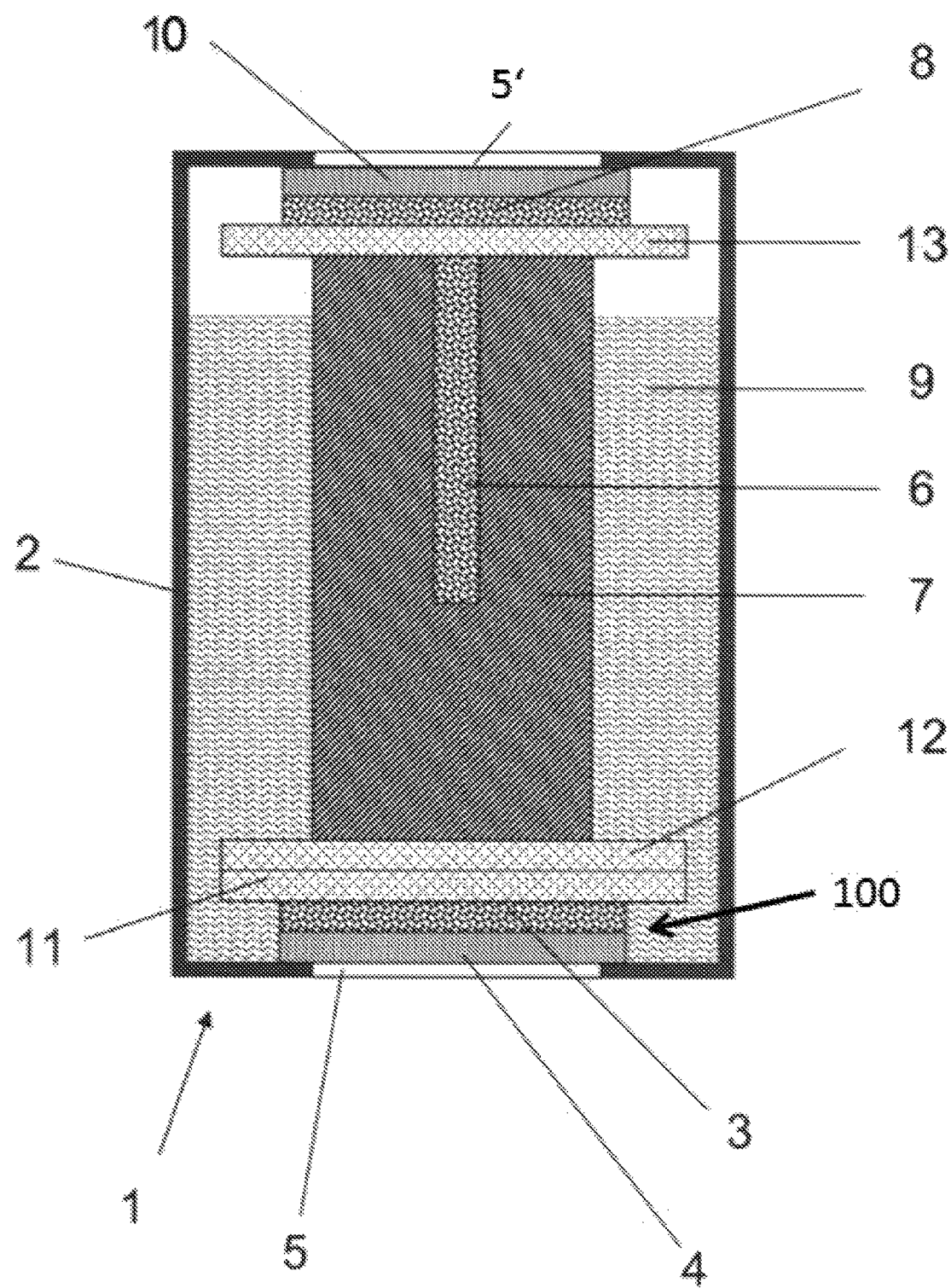
FIG. 1 is a schematic view of an electrochemical gas sensor according to the present invention with an electrode according to the present invention as a measuring sensor.

Referring to the drawings, the electrochemical gas sensor 1 shown schematically in FIG. 1, in which a measuring electrode 100, an optional reference electrode 6 and an auxiliary electrode 8 are arranged. The sensor housing 2 has, furthermore, a first opening 5 and a second opening 5'. The first opening 5 is used as a gas inlet. It is located opposite the measuring electrode 100. Gas flowing in through the opening 5 can consequently reach the measuring electrode 100 directly. The second opening 5' is used as a gas outlet. It is located opposite the auxiliary electrode 100. The second opening 5' is consequently used as a gas outlet. It is located opposite the auxiliary electrode 8. Gas formed at the auxiliary electrode 8 can consequently escape from the gas sensor 1 directly through the opening 5'.

The sensor housing 2 is filled with an electrolyte 9. The electrolyte 9 covers the measuring electrode 100. Furthermore, the electrolyte 9 is in conductive contact with the auxiliary electrode 8 as well as with the reference electrode 6. A wick 7 is for this within the sensor housing 2 in the exemplary embodiment shown. The reference electrode is arranged within the wick 7 in this exemplary embodiment. Other manners of arrangement and of establishing an electrically conductive contact between the electrolyte 9 and the electrodes, especially between the electrolyte 9, the measuring element 100 and the auxiliary electrode 8, may also be provided.

The electrochemical gas sensor 1 has, in addition, a plurality of nonwovens 11, 12, 13. These are used to securely stabilize the other sensor components at a correct distance from one another. In other words, the nonwovens 11, 12, 13 hold the measuring electrode 100, the auxiliary electrode and the wick 7 with the reference electrode 6 in their positions and ensure that these components will have the desired distance from one another.

It is seen in FIG. 1 that the measuring electrode 100 consists of a graphene layer 3, which is applied to a gas-permeable membrane 4.

The auxiliary electrode 8 advantageously consists of a precious metal or also of carbon. For example, gold, platinum and/or iridium may be provided as electrode material.

The electrolyte 9 consists of sulfuric acid in a first variant. Variants in which hygroscopic alkali or alkaline earth halides may be used as conductive electrolytes. The electrolyte 9 may optionally additionally contain a mediator.

EXAMPLE 1

Preparation of an Electrode for Use in an Electrochemical Gas Sensor

An electrode for use in an electrochemical gas sensor, consisting of reduced graphene oxide, was prepared as follows. A graphene oxide dispersion was first prepared from 1 g of single-layer graphene oxide per L of distilled water. A 4.5-mL solution was taken from this and mixed with about 70 mL of 2-propyl alcohol. This dispersion was subsequently evaporated under vacuum. This dispersion was then poured over a gas-permeable membrane (PTFE membrane) with a diameter of 80 mm. The dispersing agent was then evaporated under vacuum. The graphene oxide electrode thus obtained was then placed for about 5 hours into a concentrated hydrogen iodide solution and then dried on air. The electrode obtained comprises a gas-permeable membrane (4), on which a graphene layer (3) is applied as the electrode material.

It has a resistance of 140 $\Omega$cm-1. It is seen that the graphene layer (3) is applied from a dispersion onto the gas-permeable membrane (4) and that the graphene layer is prepared by a method that comprises the steps of
a) Dispersing graphene powder in a volatile liquid,
b) Applying the graphene dispersion prepared in step b) to the gas-permeable membrane (4), and
c) Evaporating the volatile liquid.

The graphene layer (3) consists, in addition, of reduced graphene oxide.

To prepare the electrode (100), the gas-permeable membrane (4) was advantageously prepared at the beginning of the method, before the graphene oxide dispersion was applied to the gas-permeable membrane (4).

EXAMPLE 2

Detection of Propofol by Means of a Graphene Electrode

Figure 2:
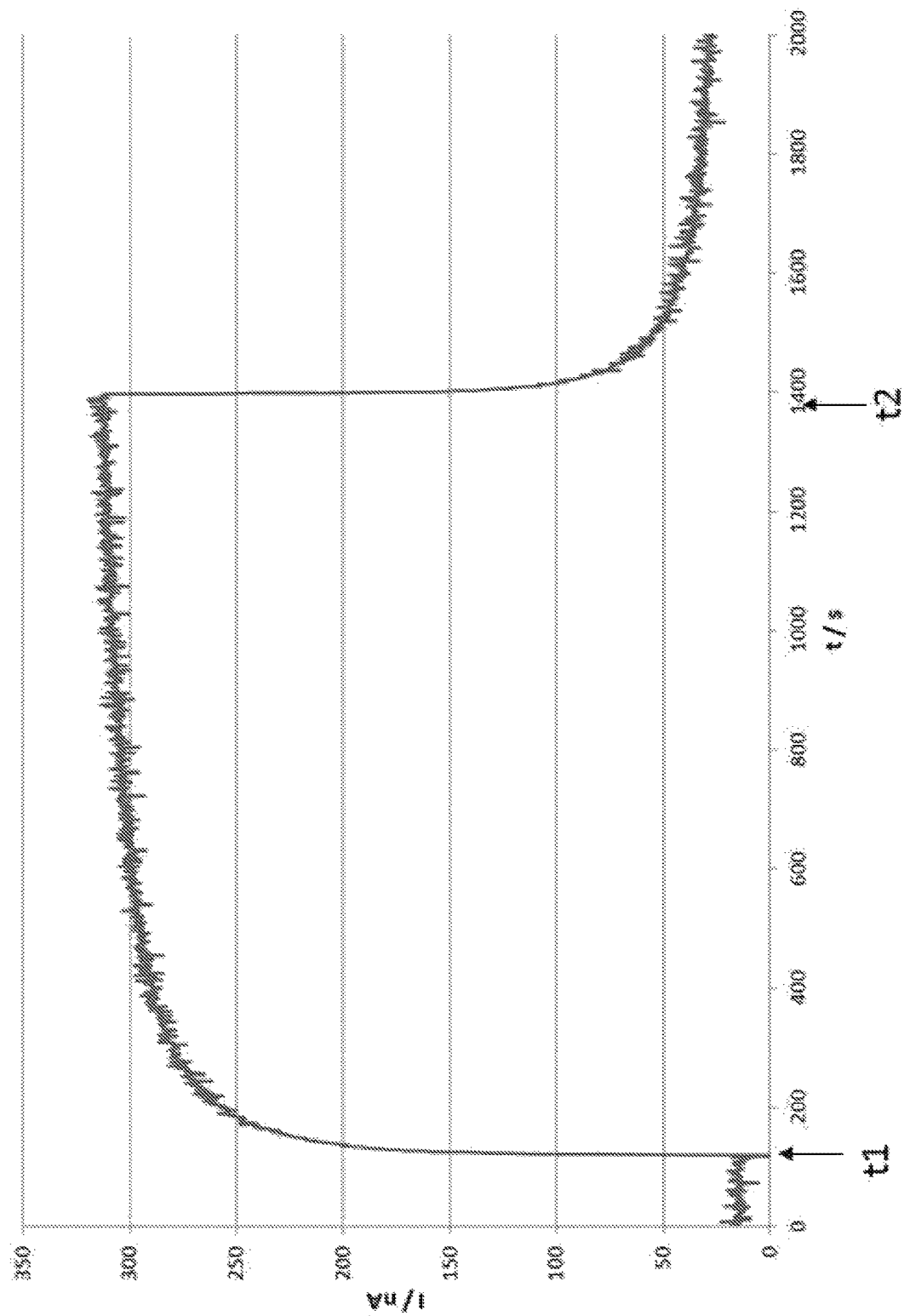
FIG. 2 is a measuring diagram, obtained by determining Propofol (20 ppb) by means of a gas sensor that uses the electrode according to the present invention according to Example 2.

An electrochemical gas sensor according to the present invention with a measuring electrode according to the present invention was tested with Propofol at a concentration of 20 ppb. The exposure to the gas was carried out at a relative humidity of 50% and an ambient temperature of 20° C. It is seen in FIG. 2 that the electrochemical gas sensor yields a nearly stepped measured curve. The gas exposure time in seconds is plotted on the abscissa and the sensor current on the ordinate. The gas exposure was started at time t1 and ended at time t2. It is seen that the sensor current changes nearly abruptly at the start of the gas exposure at time t1 and shows the reaction gas (Propofol) rapidly and reliably. After removal of the reaction gas at time t2, the gas sensor returns to the starting state just as rapidly.

EXAMPLE 3

Detection of Chlorine Dioxide by Means of a Graphene Electrode

Figure 3:
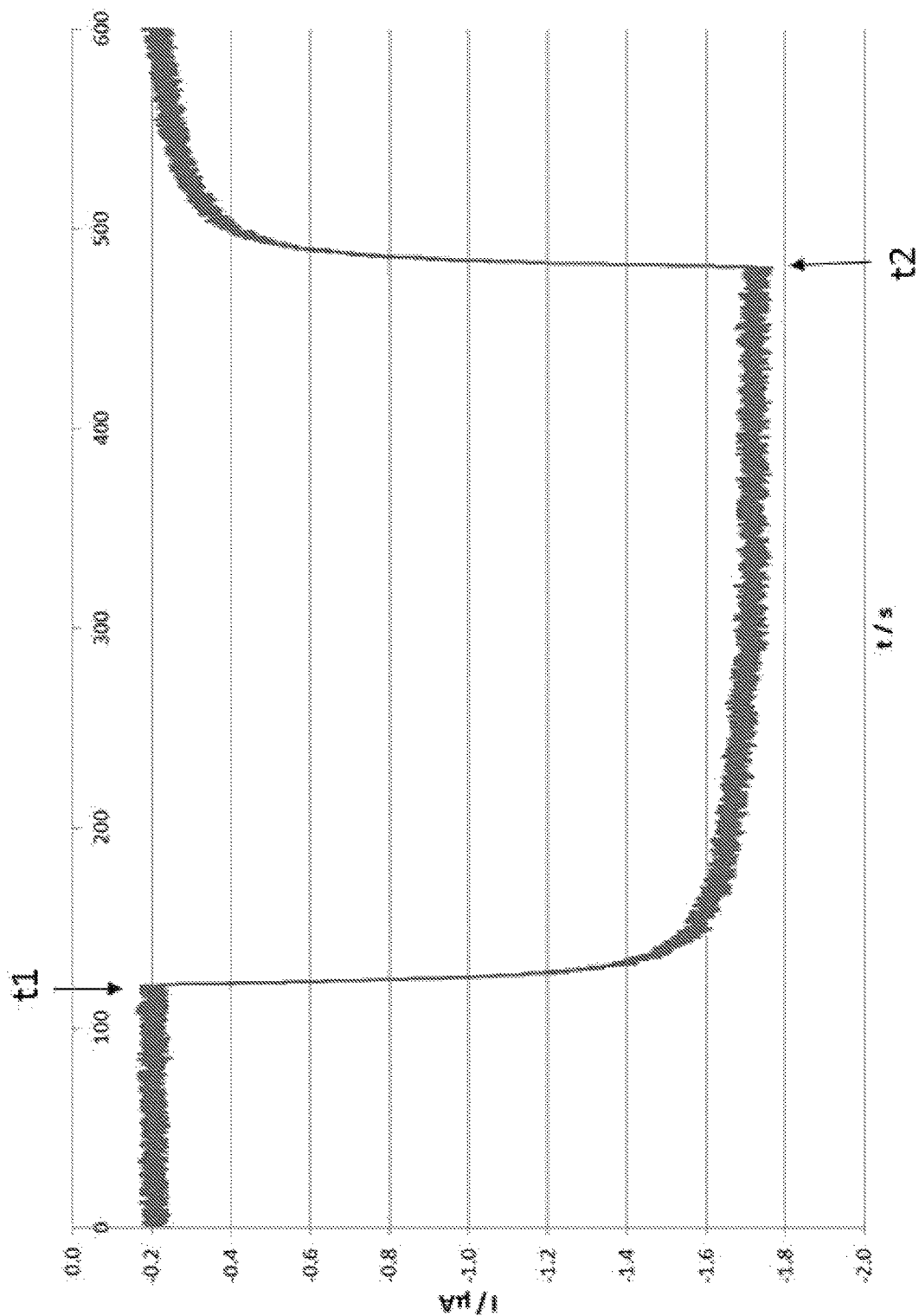
FIG. 3 is a measuring diagram obtained by determining chlorine dioxide (1.4 ppm) by means of a gas sensor that uses the electrode according to the present invention according to Example 3.

An electrochemical gas sensor according to the present invention with a measuring electrode according to the present invention was tested with chlorine dioxide at a concentration of 1.4 ppm. The gas exposure was carried out at a relative humidity of 50% and an ambient temperature of 20° C. It is seen in FIG. 3 that the electrochemical gas sensor yields a nearly stepped measured curve. The gas exposure time in seconds is plotted on the abscissa and the sensor current on the ordinate. The gas exposure was started at time t1 and ended at time t2. It is seen that the sensor current changes nearly abruptly at the beginning of the gas exposure and shows the reaction gas (Propofol) rapidly and reliably. After removal of the reaction gas at time t2, the gas sensor returns to the starting state just as rapidly.

The exemplary embodiments and variants are, of course, only examples. It is obvious that there are a large number of other variants, which are not explicitly described here, and which are likewise covered by the inventive idea and consequently fall under the protection of these claims.

While specific embodiments of the invention have been shown and described in detail to illustrate the application of the principles of the invention, it will be understood that the invention may be embodied otherwise without departing from such principles.

The invention claimed is:
1. An electrochemical gas sensor comprising:
    a sensor housing;
    an auxiliary electrode disposed in the housing; and
    electrochemical gas sensor electrode disposed in the housing, the electrochemical gas sensor electrode comprising:
        a gas-permeable membrane forming a gas-permeable membrane layer of the electrochemical gas sensor electrode; and
        a graphene layer applied on the gas-permeable membrane layer as an electrode material having a resistance lower than 10 k$\Omega$ and which is gas-permeable, wherein the graphene layer is applied to the gas-permeable membrane by a process comprising the steps of:
        dispersing graphene powder in a volatile liquid to provide a graphene dispersion; and
        applying the graphene dispersion to the gas-permeable membrane.
2. An electrochemical gas sensor in accordance with claim 1, wherein the graphene layer is in the form of a multi-layer graphene.
3. An electrochemical gas sensor in accordance with claim 1, wherein the process of applying the graphene to the gas-permeable membrane further comprises the step of evaporating the volatile liquid from the graphene dispersion applied to the gas-permeable membrane.

4. An electrochemical gas sensor in accordance with claim 1, wherein the graphene layer applied to the gas-permeable membrane consists of reduced graphene oxide.

5. An electrochemical gas sensor in accordance with claim 1, wherein the process of applying the graphene to the gas-permeable membrane further comprises the following steps:
preparing the gas-permeable membrane;
dispersing graphene oxide, as the graphene, in the volatile liquid to provide a graphene oxide dispersion as the graphene dispersion;
applying the graphene oxide dispersion to the gas-permeable membrane as a part of the step of applying the graphene dispersion to the gas-permeable membrane; and
treating the graphene oxide deposited on the gas-permeable membrane with a reducing agent such that the graphene layer consists of reduced graphene oxide.

6. An electrochemical gas sensor in accordance with claim 5, wherein the reducing agent is selected from the group consisting of hydrazine, hydrogen iodide and mixtures containing hydrazine and hydrogen iodide.

7. An electrochemical gas sensor in accordance with claim 1, wherein the process of applying the graphene to the gas-permeable membrane further comprises the following steps:
dispersing graphene oxide, as the graphene, in the volatile liquid to provide a graphene oxide dispersion as the graphene dispersion;
treating the graphene oxide dispersion with a reducing agent, so that the graphene oxide dispersion is at least partly converted into a reduced graphene oxide dispersion;
applying the reduced graphene oxide dispersion treated with the reducing agent to the gas-permeable membrane as a part of the step of applying the graphene dispersion to the gas-permeable membrane; and
evaporating the volatile liquid.

8. An electrochemical gas sensor in accordance with claim 7, wherein the reducing agent is selected from the group consisting of hydrazine, hydrogen iodide and mixtures containing hydrazine and hydrogen iodide.

9. A method for preparing an electrode for an electrochemical sensor comprising a sensor housing, an auxiliary electrode and an electrochemical gas sensor electrode, the electrochemical gas sensor electrode comprising a gas-permeable membrane and a graphene layer applied as an electrode material to the gas-permeable membrane wherein the method comprises the following steps:
preparing a graphene dispersion or a graphene oxide-containing dispersion or both a graphene dispersion and a graphene oxide-containing dispersion with a volatile liquid as a dispersing agent;
applying the dispersion to a gas-permeable membrane; and,
evaporating the volatile liquid such that the graphene or the graphene oxide or both the graphene and the graphene oxide is deposited as a graphene or graphene oxide or both a graphene and graphene oxide layer on the gas-permeable membrane to provide the electrode material, applied to the gas-permeable membrane, with a resistance lower than 10 kΩ and which is gas-permeable.

10. A method in accordance with claim 9, further comprising the step of treating the graphene oxide with a reducing agent wherein the reducing agent is used in the gaseous state or as a solution.

11. A method in accordance with claim 10, wherein the reducing agent is selected from the group comprising hydrazine, hydrogen iodide and mixtures containing hydrazine and hydrogen iodide.

12. A method in accordance with claim 10, wherein the step of treating the graphene oxide with a reducing agent occurs after the step of evaporating the volatile liquid.

13. A method in accordance with claim 10, wherein the step of treating the graphene oxide with a reducing agent occurs prior to applying the dispersion to the gas-permeable membrane.

14. A method in accordance with claim 9, further comprising measuring a gas with the electrochemical gas sensor.

15. A method in accordance with claim 14, wherein the electrochemical gas sensor is a gas sensor determining Propofol.

16. A method in accordance with claim 14, wherein the electrochemical gas sensor is a gas sensor determining chlorine dioxide.

17. An electrochemical gas sensor comprising at least one electrode comprising:
a gas-permeable membrane forming a gas-permeable membrane layer of the electrochemical gas sensor electrode; and
a graphene layer applied on the gas-permeable membrane layer as an electrode material having a resistance lower than 10 kΩ and which is gas-permeable, wherein the graphene layer is applied to the gas-permeable membrane by a process comprising the steps of:
dispersing graphene powder in a volatile liquid to provide a graphene dispersion; and
applying the graphene dispersion to the gas-permeable membrane.

18. An electrochemical gas sensor in accordance with claim 17, wherein the process of applying the graphene to the gas-permeable membrane further comprises the steps of:
preparing the gas-permeable membrane;
dispersing graphene oxide, as the graphene, in the volatile liquid to provide a graphene oxide dispersion as the graphene dispersion;
applying the graphene oxide dispersion to the gas-permeable membrane as a part of the step of applying the graphene dispersion to the gas-permeable membrane; and
treating the graphene oxide deposited on the gas-permeable membrane with a reducing agent such that the graphene layer consists of reduced graphene oxide.

19. An electrochemical gas sensor in accordance with claim 18, wherein the reducing agent is selected from the group consisting of hydrazine, hydrogen iodide and mixtures containing hydrazine and hydrogen iodide.

20. An electrochemical gas sensor in accordance with claim 17, wherein the process of applying the graphene to the gas-permeable membrane further comprises the following steps:
dispersing graphene oxide, as the graphene, in the volatile liquid to provide a graphene oxide dispersion as the graphene dispersion;
treating the graphene oxide dispersion with a reducing agent, so that the graphene oxide dispersion is at least partly converted into a reduced graphene oxide dispersion;

applying the reduced graphene oxide dispersion treated with the reducing agent to the gas-permeable membrane as a part of the step of applying the graphene dispersion to the gas-permeable membrane; and
evaporating the volatile liquid.

* * * * *